US007199232B2

(12) United States Patent
Glaab et al.

(10) Patent No.: US 7,199,232 B2
(45) Date of Patent: Apr. 3, 2007

(54) ISOLATED NUCLEIC ACID MOLECULES ENCODING A BACTERIAL URACIL TRANSPORT PROTEIN AND A BACTERIAL URACIL PHOSPHORIBOSYL-TRANSFERASE ENZYME, CELLS TRANSFORMED THEREWITH AND USES THEREOF

(76) Inventors: Warren Glaab, Merck & Co., Inc., P.O. Box 2000, Rahway, NJ (US) 07065-0907; Thomas Skopek, Merck & Co., Inc., P.O. Box 2000, Rahway, NJ (US) 07065-0907

( * ) Notice: Subject to any disclaimer, the term of this patent is extended or adjusted under 35 U.S.C. 154(b) by 371 days.

(21) Appl. No.: 10/490,463

(22) PCT Filed: Sep. 25, 2002

(86) PCT No.: PCT/US02/30435

§ 371 (c)(1),
(2), (4) Date: Mar. 23, 2004

(87) PCT Pub. No.: WO03/029407

PCT Pub. Date: Apr. 10, 2003

(65) Prior Publication Data

US 2005/0197497 A1    Sep. 8, 2005

(51) Int. Cl.
C07H 21/04    (2006.01)
C12N 1/21    (2006.01)
C12N 15/31    (2006.01)
C12N 15/63    (2006.01)
C07K 14/195    (2006.01)
C12Q 1/68    (2006.01)

(52) U.S. Cl. ............... 536/23.7; 435/6; 435/252.3; 435/320.1; 530/350

(58) Field of Classification Search ............... None
See application file for complete search history.

(56) References Cited

U.S. PATENT DOCUMENTS

| 4,394,448 A | 7/1983 | Szoka, Jr. et al. |
| 4,399,216 A | 8/1983 | Axel et al. |
| 4,405,712 A | 9/1983 | Vande Woude et al. |
| 4,619,794 A | 10/1986 | Hauser |
| 4,634,665 A | 1/1987 | Axel et al. |
| 4,650,764 A | 3/1987 | Temin et al. |
| 5,858,707 A | 1/1999 | Guimaraes et al. |

FOREIGN PATENT DOCUMENTS

| WO | WO 01/70955 | 9/2001 |
| WO | WO 02/77183 | 10/2002 |

OTHER PUBLICATIONS

Andersen et al.,"Characterization of the *upp* gene encoding uracil phosphoribosyltransferase of *Escherichia coli* K12", Eur. J. Biochem., 204:51-56 (1992).

Molloy, A., et al., "Uridine-5' Monophosphate Pyrophosphorylase Activity From *Escherichia Coli*", FEBS Letts., 5(3):211-213 (1969).
Kern et al.,"The *FURI* gene of *Saccharomyces cerevisiae*: cloning, structure and expression of wild-type and mutant alleles", Gene, 88:149-157 (1990).
Kawamura, K. et al., "Expression of *Escherichia coli* uracil phosphoribosyltransferase gene in murine colon carcinoma cells augments the antitumoral effect of 5-fluorouracil and induces protectiev immunity", Cancer Gene Therapy, 7(4):637-643 (2000).
Sunamura, M. et al., "Development of gene therapy for pancreatic cancer", Nippon Rinsho, 59:(1)98-103 (2001).
Inaba, M. et al., "Circumvention of 5-Fluorouracil Resistance in Human Stomach Cancer4 Cells by Uracil Phosphoribosyltransferase Gene Transduction", Japan J. Cancer Res., 90:349-354 (1999).
Kanai et al., "Adenovirus-mediated Transduction of *Escherichia coli* Uracil Phosphoribosyltransferase Gene Sensitizes Cancer Cells to Low Concentrations of 5-Fluorouracil", Cancer Research, 58:1946-1951 (1998).
Beaucage & Carruthers, "Deoxynucleoside Phosphoramidites—A New Class of Key Intermediates for Deoxypolynucleotide Synthesis", Tetrahedron Letters, 22(20):1859-1862 (1981).
Denhardt, David T., "A Membrane-Filter Technique for the Detection of Complementary DNA", Biochemical and Biophysical Research Communications, 23(5):641 (1966).
Friedmann, Theodore; "Progress Toward Human Gene Therapy", Science, 244:1275-1281 (1989).
Okayama & Berg, "High-Efficiency Cloning of Full-Length cDNA", Molecular and Cellular Biology, 2(2):161-170 (1982).
Wong et al., Genetics Institute, "Human GM-CSF: Molecular Cloning of the Complementary DNA and Purification of the Natural and Recombinant Proteins", Science, 228:810-815 (1985).
Urlaub et al., "Effect of Gamma Rays at the Dihydrofolate Reductase Locus: Deletions and Inversions", Somatic Cell Molecular Genetics, 12(6):555-566 (1986).
Bahouth et al., "Immunological approaches for probing receptor structure and function", Trends Pharmacol. Science, 12:338-343 (1991).
Kinsella et al., "Resistance to chemotherapeutic antimetabolites: a functon of salvage pathway involvement and cellular response to DNA damage", British Journal of Cancer, 75(7):935-945 (1997).
Grove et al., "Uptake and Metabolism of the New Anticancer Compound β-L-(-)-Dioxolane-Cytidine in Human Prostate Carcinoma DU-145 Cells", Cancer Research, 56: 4187-4191, 1996.
Griffith et al., "Nucleoside and nucleobase transport systems of mammalian cells", Biochimica et Biophysica Acta, 1286(3): 153-181, 1996.
Jund et al., "Primary structure of the uracil transport protein of *Saccharomyces cerevisiae*", European Journal of Biochemistry, 171(1-2): 417-424, 1988.
McClelland et al., "Complete genome sequence of *Salmonella enterica* serovar Typhimurium LT2", Nature, 413:852-856, 2001.

(Continued)

*Primary Examiner*—Elizabeth Slobodyansky
(74) *Attorney, Agent, or Firm*—Vineet Kohli; Joanne M. Giesser

(57) ABSTRACT

Disclosed herein are novel polynucleotides encoding one of a uracil transport protein and a uracil phosphoribosyl transferase, each being derived from *Salmonella typhimurium*. The disclosed uracil phosphoribosyl transferase protein is useful in sensitizing human cancer cells to treatment with anti-cancer agents such as 5-Fluorouracil.

8 Claims, No Drawings

OTHER PUBLICATIONS

Molchan, O.K. et al., "Isolation and Initial Characterization of the Uridine Phosphorylase from *Salmonella typhimurium*", Biochemistry (Moscow), 63(2):195-199, 1998.

Andersen, Paal Skytt et al., "Uracil Uptake in *Escherichia coli* K-12: Isolation of *uraA* Mutants and Cloning of the Gene", Journal of Bacteriology, 177(8):2008-2013, 1995.

Bork, P. et al., "Predicting Function: From Genes to Genomes and Back", Journal of Molecular Biology, 283(4):707-725, 1998.

Database GenBank Accession No. STU68765, Sep. 26, 1996.

Kawamura, Kiyoko et al., "Expression of *Escherichia coli* uracil phosphoribosyltransferase gene in murine colon carcinoma cells augments the antitumoral effect of 5-fluorouracil and induces protective immunity", Cancer Gene Therapy, 7(4):637-643, 2000.

Database GenBank Accession No. AAS56214, Mar. 14, 2004.

Database GenBank Accession No. AAU38356, Sep. 17, 2004.

Parkhill, J. et al., "Complete genome sequence of a multiple drug resistant *Salmonella enterica* serovar Typhi CT18", Nature, 413:848-852, 2001.

though effective against certain cancers, this approach is not universally applicable and as such, there exists a desperate need for new and improved anti-cancer strategies.

ISOLATED NUCLEIC ACID MOLECULES ENCODING A BACTERIAL URACIL TRANSPORT PROTEIN AND A BACTERIAL URACIL PHOSPHORIBOSYL-TRANSFERASE ENZYME, CELLS TRANSFORMED THEREWITH AND USES THEREOF

CROSS-REFERENCE TO RELATED APPLICATIONS

Not applicable.

STATEMENT REGARDING FEDERALLY-SPONSORED R&D

Not applicable.

REFERENCE TO MICROFICHE APPENDIX

Not applicable.

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are of bacterial origin, i.e., isolated from *Salmonella typhimurium*. In particular, the invention relates to isolated nucleic acid molecules, such as DNA and RNA encoding a uracil transport protein and a uracil phosphoribosyltransferase and uses thereof.

In most organisms, the biosynthesis of the purine, pyrimidine, and pyridine nucleotides, as well as the aromatic amino acids, histidine, and tryptophan, involves a group of ten enzymes known as phosphoribosyltransferases (PRTases). Each of these enzymes is highly specific for a nitrogenous base, generally aromatic, a divalent metal ion and $\alpha$-D-5-phosphoribosyl 1-pyrophosphate (PRPP). In all cases, cleavage of the pyrophosphate moiety of PRPP is accompanied by the anomeric inversion of the ribofuranose ring resulting in a $\beta$-N riboside monophosphate. In vertebrates, several PRTases exhibit a striking organ specificity while others are found in varying levels in most tissues. In all organisms, the PRTases are subcellularly confined to the soluble cytoplasmic fractions. In mammals, a single enzyme, orotate phosphoribosyltransferase (OPRTase), is responsible for the salvage of pyrimidine bases. However, in bacteria, yeast, and plant cells a uracil-specific enzyme is also found—Uracil phosphoribosyltransferase (Uracil phosphoribosyltransferase)

Uracil phosphoribosyltransferase of bacterial origin catalyzes the conversion of uracil and 5-phosphoribosyl $\alpha$-1-pyrophosphate (PRib-PP) to uridine-5'-monophosphate (UMP) and $PP_i$. See Neuhard et al., Metabolism oh Nucleotides, Nucleosides and Nucleobases in Microorganisms (Munich-Petersen A., ed.) Academic Press, New York, 95–148. Importantly, the bacterial uracil phosphoribosyltransferase, although absent in mammalian cells is nevertheless functionally equivalent to orotate phosphoribosyltransferase or uridine-5'-monophosphate synthase of mammalian cells and has a fundamental importance in the utilization of endogenous uracil formed by degradation of pyrimidine and in the utilization of exogenous uracil, cytosine and uridine for pyrimidine synthesis. This has been demonstrated in *Saccharomyces cerevisiae*, infra.

The UPP gene from *Escherichia coli* encodes for the enzyme uracil phosphoribosyltransferase and has been isolated by Anderson et al., Eur J. Biochem, 204: 51–56 (1992). (Andersen et al., 1992). Mutants of *Escherichia coli* lacking the enzyme uracil phosphoribosyltransferase but with an intact uracil transport system fail to grow on uracil as a pyrimidine source and they excrete uracil into the culture medium. See Malloy A., et al. FEBS Letts., 5: 211–213 (1969). Furthermore they are resistant to 20 µM 5-fluorouracil, this being a phenotype which has been used in the selection of UPP mutants.

The role of uracil phosphoribosyltransferase in the salvage of endogenously formed uracil and in the utilization of exogenous uracil and cytosine has been demonstrated in several microorganisms including *Escherichia coli*. The pyrimidine salvage enzymes enable the cells to utilize preformed nucleobases and nucleosides either from the growth medium or from degradation products of cellular nucleic acids.

The nucleotide sequence of the gene encoding URPTase from *Saccharomyces cerevisiae* has recently been published. See Kern, et al., *Gene*, 88: 149–157 (1990). This gene encodes a 28.7-kDa protein. The deduced amino acid sequences of the Uracil phosphoribosyltransferase from *Escherichia coli* and *Saccharomyces cerevisiae* have been compared and found to share some similarities in discrete areas despite only 32% overall identities.

Natural nucleosides and nucleobases are important metabolites and have a myriad of physiological effects in many organs, systems and species. As a result of the varied metabolic fates of nucleosides and nucleobases and their key role in nucleic acid metabolism, many analogues of these compounds have been synthesized over the past 40 years with the aim of developing clinically useful drugs. Synthetic nucleosides have important applications in chemotherapy of the leukemias and as antiviral agents, e.g. cytosine arabinoside (araC), acyclovir, azidothymidine, 5-fluorodeoxyuridine and 5-fluorouracil. New analogues of nucleobases and nucleosides acting as antimetabolites and antibiotics continue to be synthesized and evaluated for prospective therapeutic application. Some nucleosides and nucleobases can reverse the effects of particular inhibitors of de novo pyrimidine and purine synthesis such as methotrexate, 5-fluorouracil and N-phosphonoacetyl-L-aspartate.

Bacterial uracil phosphoribosyltransferase is functionally equivalent to orotate phosphoribosyltransferase or uridine-5'-monophosphate synthase of mammalian cells. These enzymes mediate the conversion of 5-fluorouracil (5-FU)[1], to 5-fluorouridine 5' monophosphate (5-FUMP). 5-fluorouridine 5' monophosphate is subsequently converted 5-FdUDP and 5-FdUMP in the mammalian de novo pyrimidine pathway. Each 5-FdUNT is an irreversible inhibitor of thymidylate synthase (Thy-A) and results in dTIP starvation and subsequent apoptosis. This conversion is one of the requisite pathways to achieve cytotoxic effects of 5-fluorouracil. See Kawamura, K et al., Cancer Gene Ther., 7: 637–43 (2000) whose data corroborate the above conclusions regarding the ability of bacterially derived uracil phosphoribosyltransferase to convert 5-fluorouracil to an active metabolite 5-fluorouridine-5'-monophosphate as does mammalian orotate phosphoribosyltransferase. It has been suggested that the bacterial uracil phosphoribosyltransferase encoding gene that is absent in mammalian cells, when expressed in tumor cells, can effectively enhances the cytotoxic effect attending 5-fluorouracil in the transduced cells.

[1] 5-FU has been approved by the FDA for the treatment of cancer. However, it is relatively toxic to patients. As such, its dose must be minimized to avoid adverse reactions. See Pinedo, et al., J. Clin. Oncol., 6: 1653–1664 (1988).

The data suggest that uracil phosphoribosyltransferase gene therapy with 5-fluorouracil can sensitize the antitumor effect of 5-fluorouracil. Consequently, this approach is a new chemosensitizing strategy for cancer gene therapy and a more feasible modality for the treatment of bladder cancer.

Researchers have also reported that infecting human colon cancer cells with an adenovirus carrying the *Escherichia coli* gene for uracil phosphoribosyltransferase makes them much more sensitive to treatment with 5-fluorouracil. The data demonstrate that the adenoviral-mediated transfer of the *Escherichia col* UPP gene enhances both the DNA- and RNA-directed activating anabolisms of 5-fluorouracil resulting in sensitizing human colon cancer cells to treatment with 5-FU, thus suggesting that "the UPRT/5-fluorouracil system can be regarded as a new biochemical modulation of fluorouracil therapy for colorectal cancer treatment." See Koyama, F et al., Eur J Cancer, 36:2403–2410 (2000).

As well, Sunamura, M. et al., Nippon Rinsho, 59: 98–103 (2001) report that the transfection of a bacterial UPP gene into pancreatic cells resulted in a significant change in the sensitivity of pancreatic cells against 5-fluorouracil. See also Adachi, Y. et al., Hum. Gene Ther., 11 :77–89 (2000). Similar results have been reported by Inaba M et al., Jpn J Cancer Res. 90: 349–354 (1999) in a human stomach cancer cell line. As well, Kanai et al., Cancer Res, 58: 1946–51 (1998) report that adenovirus-mediated transduction of *Escherichia coli* uracil phosphoribosyltransferase encoding gene resulted in a marked sensitization of colon, gastric, and pancreatic cancer cell lines. More, 5-fluorouracil treatment of human hepatoma or gastric cancer xenografts in nude mice transduced with a bacterial uracil phosphoribosyltransferase encoding gene resulted in a significant in vivo antitumor effect.

Nucleoside and nucleobase transportation is common in a large variety of organisms and has many different physiological effects (Griffith and Jarvis 1996). Physiological nucleosides and nucleobases, and most nucleoside analogues, are hydrophilic, and specialized transport systems are required for their movement into or out of cells. The presence or absence of nucleoside and nucleobase transporters in cells and organisms will have an important impact on the pharmacokinetics, and the disposition and in vivo biological activity of physiological occurring compounds as well as nucleoside and nucleobase drugs.

Several references describe that the uracil transport protein is necessary for uracil uptake at low exogenous uracil concentrations, even under conditions with high uracil phosphoribosyltransferase activity. Investigators have suggested that uracil enters the cytoplasm by facilitated diffusion across the cytoplasmic membrane where the uracil transport protein is a membrane-bound facilitator.

It is noteworthy that none of the prior art references describe the isolation of a uracil transport protein or the gene encoding this protein—uraA or a UPP gene encoding for uracil phosphoribosyltransferase from *Salmonella typhimurium*.

As such, the availability of the disclosed isolated nucleic acid molecules that will fulfill the above referenced voids in the prior art and will provide detailed information of the encoded proteins' structure and function based on predictions drawn from other sources.

In addition, the availability of the disclosed isolated nucleic acid molecules will allow for improving the therapeutic efficacy of current cancer treatment protocols as well as allowing for the development of therapeutic candidates that are capable of sensitizing cancerous cells to treatment with conventional anti-tumor drugs etc.

As well, the identity of the proteins encoded by the herein disclosed nucleic acid molecules will enable the rapid screening of a large number of compounds to identify those candidates suitable for further, in-depth studies of therapeutic applications.

SUMMARY OF THE INVENTION

The invention provides isolated nucleic acid molecules derived from *Salmonella typhimurium*, encoded proteins, including mRNAs, DNAs, cDNAs, genomic DNA, as well as antisense analogs thereof. Also provided are biologically active and diagnostically or therapeutically useful fragments thereof, as well as antibodies immunoreactive with the herein disclosed proteins.

Plasmids containing DNA encoding the invention peptides are also provided. Recombinant cells containing the above-described DNA, mRNA or plasmids are also provided herein.

Vector(s) comprising the invention nucleic acid molecules are also provided as are processes for producing the invention peptide(s) by recombinant techniques. A proposed method comprises culturing transformed prokaryotic and/or eukaryotic host cells containing nucleic acid sequences encoding the invention peptides under conditions promoting expression of the invention peptide, followed by subsequent recovery of the polypeptide(s).

In accordance with yet another aspect of the present invention, there are provided single-stranded nucleic acid probes comprising nucleic acid molecules of sufficient length to specifically hybridize to the polynucleotide sequences of the present invention.

The single-stranded nucleic acid probes and mixtures thereof provided by the present invention will enable one of ordinary skill in the art of genetic engineering to identify and clone similar polynucleotides and encoded polypeptides from any species thereby expanding the usefulness of the sequences of the invention.

The probes may be the full length sequence of the nucleic acid molecules encoding the invention peptides or fragments thereof. Typical probes are 12 to 40 nucleotides in length. Generally, the probes are complementary to the coding sequence, although probes to introns are also contemplated.

The probes may be synthesized using an oligonucleotide synthesizer such as Applied Biosystems Model 392 DNA/RNA synthesizer, and may be labeled with a detectable marker. Combinations of two or more labeled probes corresponding to different regions of the nucleic acid also may be included in kits to allow for the detection and/or analysis of the gene by hybridization.

In another aspect, the invention features assays for detecting the invention peptide.

In another aspect, the present invention provides diagnostic assays for detecting diseases related to mutations in the nucleic acid sequences encoding the invention peptide and for detecting an altered level of the encoded polypeptide.

In accordance with yet a further aspect of the present invention, there are provided processes for utilizing the invention peptide or nucleic acid molecules encoding such polypeptides for in vitro purposes such as synthesis of DNA and manufacture of DNA vectors.

Also provided are methods for identifying cells that express the invention peptide.

The availability of the invention polypeptides-specific antibodies makes possible the application of the technique of immunohistochemistry to monitor the distribution and expression density of the invention peptide (e.g., in normal vs diseased brain tissue). Such antibodies could also be employed for diagnostic and therapeutic applications. This antibody is preferably capable of neutralizing a biological activity of uracil transport protein or the Uracil phosphoribosyltransferase.

The ability to test either or both of the invention peptides with a variety of potential agonists or antagonists provides additional information with respect to the function and activity of either or both of the invention peptides and should lead to the identification and design of compounds that are capable of very specific interaction with human counterparts of the invention peptides, if any.

Further in relation to drug development and therapeutic treatment of various disease states, the availability of DNAs encoding the invention peptides enables identification of any alterations in such genes (e.g., mutations) which may correlate with the occurrence of certain functions heretofore unknown.

As noted, supra, 5-fluorouracil has been approved for the treatment of cancer. However, a chief drawback attending its use is its relative toxicity. In accordance with still another embodiment of the invention, there are provided processes of administering the invention nucleic acid encoding uracil phosphoribosyltransferase to host cells responsive to treatment with 5-fluorouracil in an amount sufficient to improve the therapeutic efficacy of the 5-fluorouracil. This effect is achieved by the ability of the Uracil phosphoribosyltransferase to convert the 5-fluorouracil to its non-toxic metabolite 5-fluorouridine 5' monophosphate. Thus, it is believed that the novel uracil phosphoribosyltransferase encoding gene of the invention will pave the path for a more feasible modality for the treatment of human cancers.

The present invention is described in the following Experimental Details Section, which is set forth to aid in an understanding of the invention, and should not be construed to limit in any way the invention as defined in the claims which follow thereafter. Other features and advantages of the invention will be apparent to those of skill in the art upon further study of the specification and claims.

DETAILED DESCRIPTION OF THE INVENTION

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

All publications mentioned herein are incorporated herein by reference for the purpose of describing and disclosing the methodologies, vectors etc which are reported in the publications that might be used in connection with the invention. Nothing herein is to be construed as an admission that the invention is not entitled to antedate such disclosure by virtue of prior invention.

In the description that follows, a number of terms used in the field of recombinant DNA technology are extensively utilized. In order to provide a clearer and consistent understanding of the specification and claims, including the scope to be given such terms, the following definitions are provided.

The present invention provides isolated nucleic acid molecules that encode a novel uracil transport protein and a uracil phosphoribosyltransferase, each derived from *Salmonella typhimurium*. Specifically, isolated DNA encoding the invention peptides are described as are recombinant messenger RNA (mRNA). Splice variants of the isolated DNA's are also described.

"Invention nucleic acid(s)" and "nucleic acid molecules" are used interchangeably and refer to the nucleic acid molecules of the invention that encode the invention peptides.

"Polypeptide" or "peptide" or "protein" refers to a polymer of amino acid residues and to variants and synthetic analogs of the same and are used interchangeably herein. Thus, these terms apply to amino acid polymers in which one or more amino acid residues is a synthetic non-naturally occurring amino acid, such as a chemical analog of a corresponding naturally occurring amino acid, as well as to naturally occurring amino acid polymers. The invention peptide is the preferred polypeptide.

The term "amino acid sequence" as used herein refers to an oligopeptide, peptide, polypeptide, or protein sequence, and fragments or portions thereof, and to naturally occurring or synthetic molecules.

The term "invention peptide" refers to the polypeptides encoded by the invention nucleic acid molecules. Variants and fragments are also included.

As used herein, "uracil phosphoribosyltransferase gene" or "UPP" refers to a uracil phosphoribosyltransferase gene derived from *Salmonella typhimurium* that is encoded by a nucleic acid molecule of SEQ ID NO. 1. It also includes nucleic acid molecule that hybridizes under high stringency conditions to the nucleotide sequences disclosed herein. Such nucleic acid molecule can be characterized in a number of ways, for example—the DNA may encode the amino acid sequence set forth in SEQ ID NO. 2, or the DNA may include the nucleotide sequence as set forth in SEQ ID NO. 1. The coding sequence for the UPP is from nucleotides 929–2218 as contained in FIG. 1 that encode the protein of SEQ ID NO: 2 (429 amino acids encoded by 1290 base pairs).

Typically, unless the UPP gene arises as a splice variant, the disclosed UPP DNA will share substantial sequence homology (i.e., greater than about 90%), with the UPP gene described herein. DNA or RNA encoding a splice variant may share less than 90% overall sequence homology with the DNA or RNA provided herein, but such a splice variant would include regions of nearly 100% homology to the disclosed DNAs.

As used herein, "uracil transport gene" or "uraA" refers to a uracil transport protein encoding gene derived from *Salmonella typhimurium* that is encoded by a nucleic acid molecule of SEQ ID NO. 1 or one that hybridizes under high stringency conditions to the nucleotide sequence of SEQ ID NO. 1. Such nucleic acid molecule can be characterized in a number of ways, for example—the DNA may encode the amino acid sequence set forth in SEQ ID NO. 3, or the DNA may include the nucleotide sequence as set forth in SEQ ID NO. 1. Typically, the start and stop codons are listed in FIG. 1. The arbitrary numbers for the entire sequence are nucleotides 1–2520, the coding sequence for the uracil transport protein of SEQ ID NO:2 being defined by nucleotides 215 to 841, for a total of 627 base pairs that encode for a 208 amino acid protein.

The nucleic acid molecules described herein are useful for producing invention peptides when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of a UPP or uraA encoding gene or mRNA transcript in a given sample.

The nucleic acid molecules described herein, and fragments thereof, are also useful as primers and/or templates in a PCR reaction for amplifying genes encoding the invention peptides described herein.

A "gene" refers to a nucleic acid molecule whose nucleotide sequence codes for a polypeptide molecule. Genes may be uninterrupted sequences of nucleotides or they may include such intervening segments as introns, promoter regions, splicing sites and repetitive sequences. A gene can be either RNA or DNA. A preferred gene is one that encodes the invention peptide.

The term "nucleic acid" or "nucleic acid molecule" is intended for ribonucleic acid (RNA) or deoxyribonucleic acid (DNA), probes, oligonucleotides, fragment or portions thereof, and primers. DNA can be either complementary DNA (cDNA) or genomic DNA, e.g. a gene encoding the invention peptide.

Unless otherwise indicated, a nucleotide defines a monomeric unit of DNA or RNA consisting of a sugar moiety (pentose), a phosphate group, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Each "nucleotide sequence" set forth herein is presented as a sequence of deoxyribonucleotides (abbreviated A, G, C and T). However, by "nucleotide sequence" of a nucleic acid molecule is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO. 1 set forth using deoxyribonucleotide abbreviations is intended to indicate an RNA molecule having a sequence in which each deoxyribonucleotide A, G or C of SEQ ID NO. 1 has been replaced by the corresponding ribonucleotide A, G or C, and each deoxyribonucleotide T has been replaced by a ribonucleotide U.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

Similarly, as used herein, "recombinant" as a modifier of DNA, RNA, polypeptides or proteins means that the DNA, RNA, polypeptides or proteins so designated have been prepared by the efforts of human beings, e.g., by cloning, recombinant expression, and the like. Thus as used herein, recombinant proteins, for example, refers to proteins produced by a recombinant host, expressing DNAs which have been added to that host through the efforts of human beings.

In defining nucleic acid sequences, all subject nucleic acid sequences capable of encoding substantially similar amino acid sequences are considered substantially similar or are considered as comprising substantially identical sequences of nucleotides to the reference nucleic acid sequences disclosed herein.

In practice, the term "substantially the same sequence" means that DNA or RNA encoding two proteins hybridize under moderately stringent conditions and encode proteins that have the same sequence of amino acids or have changes in sequence that do not alter their structure or function.

Nucleotide sequence "similarity" is a measure of the degree to which two polynucleotide sequences have identical nucleotide bases at corresponding positions in their sequence when optimally aligned (with appropriate nucleotide insertions or deletions). Sequence similarity or percent similarity can be determined, for example, by comparing sequence information using sequence analysis software such as the GAP computer program, version 6.0, available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math. 2:482, 1981).

As used herein, "substantially identical sequences of nucleotides" share at least about 90% identity, and substantially identical amino acid sequences share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

The present invention also encompasses nucleic acids which differ from the nucleic acids shown in SEQ ID NOs:1, but which have the same phenotype. Phenotypically similar nucleic acids are also referred to as "functionally equivalent nucleic acids".

As used herein, the phrase "functionally equivalent nucleic acids" encompasses nucleic acids characterized by slight and non-consequential sequence variations that will function in substantially the same manner to produce the same protein product(s) as the nucleic acids disclosed herein.

Functionally equivalent sequences will function in substantially the same manner to produce substantially the same compositions as the nucleic acid and amino acid compositions disclosed and claimed herein. In particular, functionally equivalent DNAs encode proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

In particular, functionally equivalent nucleic acids encode polypeptides that are the same as those disclosed herein or that have conservative amino acid variations, or that are substantially similar to one having the amino acid sequence as set forth in SEQ. ID. NO:2 or 3.

For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding the invention polypeptides that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in SEQ ID NO. 2 or 3.

Thus, an exemplary nucleic acid encoding an invention polypeptide may be selected from:

(a) DNA encoding the amino acid sequence set forth in SEQ ID NO. 2 or 3.

(b) DNA that hybridizes to the DNA of (a) under moderately stringent conditions, wherein said DNA encodes biologically active uracil transport protein of the invention or a uracil phosphoribosyltransferase enzyme of the invention; or (c) DNA degenerate with respect to either (a) or (b) above.

As used herein, the term "degenerate" refers to codons that differ in at least one nucleotide from that of SEQ ID NO:1, but encode the same amino acids as that set forth in SEQ ID NOs. 2 or 3. For example, codons specified by the triplets "UCU", "UCC", "UCA", and "UCG" are degenerate with respect to each other since all four of these codons encode the amino acid serine.

As used herein, reference to the nucleotide sequence of SEQ ID NO; 1 generally refers to the coding sequences encoding each or either of the invention peptides.

A "fragment" of a nucleic acid molecule or nucleotide sequence is a portion of the nucleic acid that is less than full-length and comprises at least a minimum length capable of hybridizing specifically with the nucleotide sequence of SEQ ID NO. 1 under stringent hybridization conditions, preferably to either or both of the coding sequences disclosed therein. The length of such a fragment is preferably 15–17 nucleotides or more.

A "variant" nucleic acid molecule or DNA molecule refers to DNA molecules containing minor changes in the native nucleotide sequence encoding the invention polypeptide(s) (coding portion), i.e., changes in which one or more nucleotides of a native sequence is deleted, added, and/or substituted, preferably while substantially maintaining the biological activity of the native nucleic acid molecule, it being understood that such changes are in either or both of the coding region specified in SEQ ID NO:1. Variant DNA molecules can be produced, for example, by standard DNA mutagenesis techniques or by chemically synthesizing the variant DNA molecule or a portion thereof. Generally, differences are limited so that the nucleotide sequences of the reference and the variant are closely similar overall and, in many regions, identical.

Changes in the nucleotide sequence of a variant polynucleotide may be silent. That is, they may not alter the amino acids encoded by the polynucleotide. Where alterations are limited to silent changes of this type, a variant will encode a polypeptide with the same amino acid sequence as the reference.

Alternatively, the changes may be "conservative." Conservative variants are changes in the nucleotide sequence (either or both of the coding region or sequence/protein-coding region) that may alter the amino acid sequence of a polypeptide encoded by the reference polynucleotide. Such nucleotide changes may result in amino acid substitutions, additions, deletions, fusions and truncations in the polypeptide encoded by the reference sequence. Thus, conservative variants are those changes in the protein-coding region of the gene that result in conservative change in one or more amino acid residues of the polypeptide encoded by the nucleic acid sequence, i.e. amino acid substitution.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

Preferably, a variant form of the preferred nucleic acid molecule has at least 70%, more preferably at least 80%, and most preferably at least 90% nucleotide sequence similarity with the native gene encoding the invention peptide.

"Primer" or "nucleic acid polymerase primer(s)" refers to an oligonucleotide, whether natural or synthetic, capable of acting as a point of initiation of DNA synthesis under conditions in which synthesis of a primer extension product complementary to a nucleic acid strand is initiated, i.e., in the presence of four different nucleotide triphosphates and an agent for polymerization (i.e., DNA polymerase or reverse transcriptase) in an appropriate buffer and at a suitable temperature. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template, but must be sufficiently complementary to hybridize with a template. A primer can be labeled, if desired.

"Identity" or "homology" with respect to the invention peptide is defined herein as the percentage of amino acid residues in the candidate sequence that are identical with the residues in one of SEQ ID NOs. 2 or 4, after aligning the sequences and introducing gaps, if necessary, to achieve the maximum percent homology, and not considering any conservative substitutions as part of the sequence identity. No N- nor C-terminal extensions, deletions nor insertions shall be construed as reducing identity or homology.

As used herein, a "variant" of the invention peptide refers to a polypeptide having an amino acid sequence with one or more amino acid substitutions, insertions, and/or deletions compared to the sequence of the invention peptide. Generally, differences are limited so that the sequences of the reference (invention peptide) and the variant are closely similar overall, and in many regions, identical. Such variants are generally biologically active and necessarily have less than 100% sequence identity with the polypeptide of interest.

In a preferred embodiment, the biologically active variant has an amino acid sequence sharing at least about 70% amino acid sequence identity with the invention peptide, preferably at least about 75%, more preferably at least about 80%, still more preferably at least about 85%, even more preferably at least about 90%, and most preferably at least about 95%. Amino-acid substitutions are preferably substitutions of single amino-acid residues.

A "fragment" of the invention peptide (reference protein) is meant to refer to a protein molecule which contains a portion of the complete amino acid sequence of the wild type or reference protein.

Complementary DNA clones encoding the invention peptide may be prepared from the DNA provided. The nucleic acid clones provided herein may be used to isolate genomic clones encoding the invention peptide and to isolate any splice variants by screening libraries prepared from different sources.

Alternatively, the library may be screened with a suitable probe. Thus, one means of isolating a nucleic acid encoding the invention peptide is to probe a bacterial genomic library with a natural or artificially designed nucleic acid probe using methods well known in the art. Nucleic acid probes derived from the invention peptide encoding gene(s) are particularly useful for this purpose. Examples of nucleic acids are RNA, cDNA, or isolated genomic DNA encoding the invention peptides. Such nucleic acids may include, but are not limited to, nucleic acids having substantially the same nucleotide sequence as set forth in SEQ ID NO. 1, preferably the coding regions contained therein or one encoding the amino acid sequence as set forth in SEQ ID NO. 2 or 3.

Nucleic acid amplification techniques, which are well known in the art, can be used to locate splice variants of the invention peptide. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns that correspond to different splice variants of transcripts encoding the invention peptide. Techniques for nucleic-acid manipulation are described generally in, for example, Sambrook et al. (1989) and Ausubel et al. (1987, with periodic updates). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

As used herein, a "splice variant" refers to variant invention peptide(s)-encoding nucleic acid(s) produced by differential processing of primary transcript(s) of genomic DNA, resulting in the production of more than one type of mRNA. cDNA derived from differentially processed primary transcript will encode the invention peptide(s) that have regions of complete amino acid identity and regions having different amino acid sequences. Thus, the same genomic sequence can lead to the production of multiple, related mRNAs and proteins. Both the resulting mRNAs and proteins are referred to herein as "splice variants".

As used herein, a nucleic acid "probe" is single-stranded DNA or RNA, or analog thereof, that has a sequence of nucleotides that includes at least 14, preferably at least 20, more preferably at least 50, contiguous bases that are the same as or the complement of any 14 or more contiguous bases set forth in any of SEQ ID NO. 1, preferably the coding regions contained therein. In addition, the entire cDNA encoding region of the invention polypeptides, or the entire sequence corresponding to SEQ ID NO. 1 may be used as a probe.

Presently preferred probe-based screening conditions comprise a temperature of about 37° C., a formamide concentration of about 20%, and a salt concentration of about 5× standard saline citrate (SSC; 20×SSC contains 3M sodium chloride, 0.3M sodium citrate, pH 7.0). Such conditions will allow the identification of sequences which have a substantial degree of similarity with the probe sequence, without requiring perfect homology.

Preferably, hybridization conditions will be selected which allow the identification of sequences having at least 70% homology with the probe, while discriminating against sequences which have a lower degree of homology with the probe. As a result, nucleic acids having substantially the same nucleotide sequence as the sequence of nucleotides set forth in SEQ ID NO. 1 are obtained.

After screening the library, positive clones are identified by detecting a hybridization signal; the identified clones are characterized by restriction enzyme mapping and/or DNA sequence analysis, and then examined, by comparison with the sequences set forth herein, to ascertain whether they include DNA encoding the entire invention peptide. If the selected clones are incomplete, they may be used to rescreen the same or a different library to obtain overlapping clones. If desired, the library can be rescreened with positive clones until overlapping clones that encode an entire invention peptide are obtained. If the library is a cDNA library, then the overlapping clones will include an open reading frame. If the library is genomic, then the overlapping clones may include exons and introns. In both instances, complete clones may be identified by comparison with the DNA and encoded proteins provided herein.

Thus, the nucleic acid probes are useful for various applications. On the one hand, they may be used as PCR primers for amplification of nucleic acid molecules according to the invention. On the other hand, they can be useful tools for the detection of the expression of molecules according to the invention in target tissues, for example, by in-situ hybridization or Northern-Blot hybridization.

The probes of the invention may be labeled by methods well-known in the art, as described hereinafter, and used in various diagnostic kits.

A "label" refers to a compound or composition that facilitates detection of a compound or composition with which it is specifically associated, which can include conferring a property that makes the labeled compound or composition able to bind specifically to another molecule. "Labeled" refers to a compound or composition that is specifically associated, typically by covalent bonding but non-covalent interactions can also be employed to label a compound or composition, with a label. Thus, a label may be detectable directly, i.e., the label can be a radioisotope (e.g., $^3$H, $^{14}$C, $^{32}$P, $^{35}$S, $^{125}$I, $^{131}$I) or a fluorescent or phosphorescent molecule (e.g., FITC, rhodamine, lanthanide phosphors), or indirectly, i.e., by enzymatic activity (e.g., horseradish peroxidase, beta-galactosidase, luciferase, alkaline phosphatase) or by its ability to bind to another molecule (e.g., streptavidin, biotin, an antigen, epitope, or antibody). Incorporation of a label can be achieved by a variety of means, ie., by use of radiolabeled or biotinylated nucleotides in polymerase-mediated primer extension reactions, epitope-tagging via recombinant expression or synthetic means, or binding to an antibody.

Labels can be attached directly or via spacer arms of various lengths, i.e., to reduce steric hindrance. Any of a wide variety of labeled reagents can be used for purposes of the present invention. For instance, one can use one or more labeled nucleoside triphosphates, primers, linkers, or probes. A description of immunofluorescent analytic techniques is found in DeLuca, "Immunofluorescence Analysis", in Antibody As a Tool, Marchalonis et al., eds., John Wiley & Sons, Ltd., pp. 189–231 (1982), which is incorporated herein by reference.

The term label can also refer to a "tag", which can bind specifically to a labeled molecule. For instance, one can use biotin as a tag and then use avidinylated or streptavidinylated horseradish peroxidase (HRP) to bind to the tag, and then use a chromogenic substrate (e.g., tetramethylbenzamine) to detect the presence of HRP. In a similar fashion, the tag can be an epitope or antigen (e.g., digoxigenin), and an enzymatically, fluorescently, or radioactively labeled antibody can be used to bind to the tag.

In one embodiment of the present invention, cDNAs encoding the invention peptides disclosed herein include substantially the same nucleotide sequence as set forth in SEQ ID NO. 1. Preferred cDNA molecules encoding the invention proteins include the same nucleotide sequence as that set forth in SEQ ID NO. 1, preferably the coding regions described therein.

Another embodiment of the invention contemplates nucleic acid(s) having substantially the same nucleotide sequence as the reference nucleotide sequence that encodes substantially the same amino acid sequence as that set forth in SEQ ID NO. 2 or 3.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C. - 16.6(\log_{10}[Na^+]) + 0.41(\%G+C) - 600/1,$$

where 1 is the length of the hybrids in nucleotides. $T_m$ decreases approximately 1°–1.50° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formarnmide, 5×Denhart's solution, 5×SSPE, 0.2% SDS at 42° C., followed by washing in 0.2×SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.

The phrase "low stringency hybridization" refers to conditions equivalent to hybridization in 10% formamide, 5×Denhart's solution, 6×SSPE, 0.2% SDS at 42° C., followed by washing in 1×SSPE, 0.2% SDS, at 50° C.

Denhardt's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20× stock solution by dissolving 175.3 g of NaCl, 27.6 g of $NaH_2PO_4$ and 7.4 g EDTA in 800 ml of water, adjusting the pH to 7.4, and then adding water to 1 liter. Denhardt's solution (see, Denhardt (1966) Biochem. Biophys. Res. Commun. 23:641) can be prepared, for example, as a 50× stock solution by mixing 5 g Ficoll (Type 400, Pharmacia LKB Biotechnology, INC., Piscataway N.J.), 5 g of polyvinylpyrrolidone, and 5 g bovine serum albumin (Fraction V; Sigma, St. Louis Mo.), and then adding water to 500 ml and filtering to remove particulate matter.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NO. 1.

The invention nucleic acids can be produced by a variety of methods well-known in the art, e.g., the methods described herein, employing PCR amplification using oligonucleotide primers from various regions of SEQ ID NO. 1 and the like.

As used herein, "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

An example of the means for preparing the invention polypeptide(s) is to express nucleic acids encoding the invention polypeptide in a suitable host cell, such as a bacterial cell, using methods well known in the art, and recovering the expressed polypeptide, again using well-known methods. Invention polypeptides can be isolated directly from cells that have been transformed with expression vectors comprising nucleic acid encoding the invention peptides or fragments/portions thereof.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) Molecular *Cloning: A Laboratory Manual*, Second Edition, Cold Spring Harbor Laboratory Press). Suitable means for introducing (transducing) expression vectors containing invention nucleic acid constructs into host cells to produce transduced recombinant cells (i.e., cells containing recombinant heterologous nucleic acid) are well-known in the art (see, for review, Friedmann, 1989, Science, 244:1275–1281; Mulligan, 1993, Science, 260: 926–932, each of which are incorporated herein by reference in their entirety).

Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The heterologous nucleic acid can optionally include sequences which allow for its extrachromosomal (i.e., episomal) maintenance, or the heterologous nucleic acid can be donor nucleic acid that integrates into the genome of the host. Recombinant cells can then be cultured under conditions whereby the invention peptide(s) encoded by the DNA is (are) expressed. Preferred cells include mammalian cells (e.g., HEK 293, CHO and Ltk- cells), yeast cells (e.g., methylotrophic yeast cells, such as *Pichia pastoris*), bacterial cells (e.g., *Escherichia coli*), and the like.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

Exemplary eukaryotic and/or prokaryotic expression vectors include eukaryotic cassettes, such as the pSV-2 gpt system (Mulligan et al., 1979, Nature, 277:108–114); the Okayama-Berg system (Mol. Cell Biol., 2:161–170), the expression cloning vector described by Genetics Institute (1985, Science, 228:810–815), and a variety of commercially available plasmid vectors such as pUC or pBC. Each of these plasmid vectors are capable of promoting expression of the invention protein of interest.

As used herein, "heterologous or foreign DNA and/or RNA" are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes the invention peptides.

In preferred embodiments, DNA is ligated into a vector, and introduced into suitable host cells to produce transformed cell lines that express the invention peptide, or a fragment thereof. The resulting cell lines can then be produced in quantity for reproducible quantitative analysis of the effects of drugs on receptor function.

In other embodiments, mRNA may be produced by in vitro transcription of DNA encoding the invention peptide. This mRNA can then be injected into *Xenopus* oocytes where the RNA directs the synthesis of the invention peptide. Alternatively, the invention-encoding DNA can be directly injected into oocytes for expression of a functional invention peptide. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can express recombinant or heterologous uracil transport proteins or uracil phosphoribosyltransferase enzyme(s) encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney cells, African green monkey cells and other such cells known to those of skill in the art), amphibian cells (e.g., *Xenopus laevis* oocytes), yeast cells (e.g., *Saccharomyces cerevisiae, Pichia pastoris*), and the like. Exemplary cells for expressing injected RNA transcripts include *Xenopus laevis* oocytes. Cells that are preferred for transfection of DNA are known to those of skill in the art or may be empirically identified, and include HEK 293; Ltk- cells; COS-7 cells ; and DG44 cells (dhrf- CHO cells; see, e.g., Urlaub et al. (1986) *Cell. Molec. Genet.* 12:555). Other mammalian expression systems, including commercially available systems and other such systems known to those of skill in the art, for expression of DNA encoding the invention peptide provided herein are presently preferred.

Nucleic acid molecules may be stably incorporated into cells or may be transiently introduced using methods known in the art. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To produce such cells, the cells should be transfected with a sufficient concentration of invention peptide-encoding nucleic acids to form the invention peptide(s) that are encoded by heterologous DNA. The precise amounts and ratios of DNA encoding the invention peptides may be empirically determined and optimized for a particular cells and assay conditions.

Heterologous DNA may be maintained in the cell as an episomal element or may be integrated into chromosomal DNA of the cell. The resulting recombinant cells may then be cultured or subcultured from such a culture or a subculture thereof. Methods for transfection, injection and culturing recombinant cells are known to the skilled artisan. Similarly, the invention peptide(s) may be purified using protein purification methods known to those of skill in the art. For example, antibodies or other ligands that specifically bind to the invention peptides may be used for affinity purification of the invention peptides.

In accordance with the above, host cells are transfected with DNA encoding the invention peptide. Using methods such as northern blot or slot blot analysis, transfected cells that contain invention peptide encoding DNA or RNA can be selected. Transfected cells can also be analyzed to identify those that express the invention peptide. As regards the uraA encoded protein, analysis can be carried out, for example, by measuring the ability of cells to bind its binding partner, i.e., antibodies immunoreactive with a bacterial uracil transport protein.

As used herein, activity of the invention peptides refers to any activity characteristic of a uracil transport protein or a uracil phosphoribosyltransferase derived from *Salmonella typhimurium*. Such activity may be measured by any method known to those of skill in the art, such as, for example, assays that measure radio-labeled uracil uptake (uracil transport activity) and the direct measurement of uracil and uridine by gas chromatography/mass spectometry (uracil conversion to uridine by uracil phosphoribosyltransferase).

The invention peptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

Also provided are antisense oligonucleotides having a nucleotide sequence capable of binding specifically with any portion of an mRNA that encodes any one of the invention peptides so as to prevent translation of the mRNA. The antisense oligonucleotide may have a sequence capable of binding specifically with any portion of the sequence of the cDNA encoding the invention polypeptides.

In accordance with yet another embodiment of the present invention, there are provided anti-invention peptide(s) antibodies i.e, uracil transport protein—or uracil phosphoribosyltransferase specific-antibodies having specific affinity for either of the invention peptides. Active fragments of antibodies are encompassed within the definition of "antibody".

Such antibodies can be produced by methods known in the art using invention polypeptides, proteins or portions thereof as antigens. For example, polyclonal and monoclonal antibodies can be produced by methods well known in the art, as described, for example, in Harlow and Lane, Antibodies: A Laboratory Manual (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., Trends Pharmacol. Sci. 12:338 (1991); Ausubel et al., Current Protocols in Molecular Biology (John Wiley and Sons, N.Y. (1989) which are incorporated herein by reference).

Antibody so produced can be used, inter alia, in diagnostic methods and systems to detect the level of the invention peptide(s) present in a sample.

Such antibodies can also be used for the immunoaffinity or affinity chromatography purification of the invention polypeptides. In addition, methods are contemplated herein for detecting the presence of invention polypeptides on the surface of a cell comprising contacting the cell with an antibody that specifically binds to at least one invention polypeptide, under conditions permitting binding of the antibody to the polypeptide, detecting the presence of the antibody bound to the cell, and thereby detecting the presence of invention polypeptide on the surface of the cell. With respect to the detection of such polypeptides, the antibodies can be used for in vitro diagnostic or in vivo imaging methods.

Immunological procedures useful for in vitro detection of invention polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures, which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

"Immunologically active fragment(s)" of the invention peptides are also embraced by the invention. Such fragments are those proteins that are capable of raising antibodies specific for any of the two disclosed invention peptides in a target immune system (e.g., murine or rabbit) or of competing with the native peptides for binding to uracil transport—or uracil phosphoribosyltransferase—specific antibodies, and is thus useful in immunoassays for the presence of, for example, human orotate phosphoribosyltransferase in a biological sample.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention peptides.

In accordance with another embodiment of the present invention, there are provided diagnostic systems, preferably in kit form, comprising at least one invention nucleic acid in a suitable packaging material. The diagnostic nucleic acids are derived from the invention peptide-encoding nucleic acids described herein. In one embodiment, for example, the diagnostic nucleic acids are derived from SEQ ID NO. 1. In another, the nucleic acid is derived from the coding regions described therein. Invention diagnostic systems are useful for assaying for the presence or absence of nucleic acid encoding the invention peptide in either genomic DNA or in transcribed nucleic acid (such as mRNA or cDNA) encoding the invention peptide.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic probes and/or primers into kit form in combination with appropriate buffers and solutions for the practice of the invention methods as described herein.

In another aspect, the herein disclosed invention nucleic acids will be useful in a microbial forward mutation assay in *Salmonella typhimurium* to assess the mutagenic potential of exogenous and endogenous compounds. The assay can score mutations in either the uracil phosphoribosyltransferase or the uracil transport genes, which can be selected by resistance to the toxic effects of 5-fluorouracil, a substrate for both enzymes. This microbial mutation assay may provide a convenient and rapid mutation assay suitable for high throughput screening of test compounds.

The failure of currently available chemotherapeutic regimes to cure most types of cancer is predominantly due to drug resistance. Significantly, the chemotherapeutic antimetabolite 5-fluorouracil inhibits key steps in the pathways principally of pyrimidine biosynthesis. In simple terms inhibition of these pathways leads to a shortage of the building blocks for DNA, the resultant inhibition of DNA synthesis and, depending on cell type, the rapid or eventual induction of DNA strand breaks. The detailed mechanisms of action of 5-fluorouracil has already been extensively reviewed by Kinsella et al., *Br. J. Cancer,* 75: 935–945 and references therein.

As a consequence of the above recitation, the invention provides methods for improving sensitivity of cancerous cells to treatment with anti-metabolite such as 5-fluorouracil. Indeed, an embodiment of the invention is drawn to a method for improving the therapeutic efficacy of an anti-cancer agent that includes transfecting cells responsive to treatment with the agent, i.e., cancer cells of the bladder etc.

with a therapeutically effective amount of the nucleic acid molecule of SEQ ID NO. 1, preferably the coding regions(s) encoding the protein of SEQ ID NO; 2—uracil phosphoribosyl transferase protein or a substantially similar sequence or variant thereof sufficient to sensitize the cells for treatment with the anticancer agent.

The anticancer agent may be 5-Fluorouracil or any other agent that can be acted upon by the disclosed sequence of nucleotides that encode the protein of SEQ ID NO. 2 and converted into a non-toxic agent via a metabolite.

Likewise, another embodiment of the invention promises a method for following progress of a therapeutic regime designed to alleviate a pathological condition responsive to treatment with 5-Fluorouracil such as tumors of the bladder, etc, which provides for assaying a sample of cancerous cells prior to and after treatment (transfection of cells) with the nucleic acid molecule of that encodes the protein of SEQ ID NO. 2 or and comparing the level of the activated/non-toxic metabolite i.e., 5-fluorouridine 5' monophosphate which results from activation of 5-fluorouracil by the gene product of SEQ ID NO. 1, preferably the coding sequence encoding the uracil phosphoribosyl transferase. This is done over time and the comparisons made thereof.

Generally, an increase in the level of production of the metabolite over time is indicative of the efficacy of the treatment protocol. In other words, if, over time, the level of the metabolite increases, after the cells are transfected with the SEQ ID NO. 1, preferably the coding portion of SEQ ID NO: 1 that encodes the protein of SEQ ID NO; 2, inter alia, nucleotides 215–841 or a sequence substantially similar thereto, this suggests that the gene therapy method is successfully sensitizing the cells to treatment with the anticancer agent and thus is beneficial to the patient.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

EXAMPLE 1

Isolation of DNA Encoding Uracil Transport Protein and DNA Encoding Uracil Phosphoribosyltransferase Protein from Salmonella taphimurium Genomic DNA from *Salmonella typhimurium* TA100 was first obtained using Qiagen DNeasy Tissue Kit (catalog # 69504) as described by the manufacturer. Initial attempts to isolate the *Salmonella* UPP gene involved designing PCR primers flanking the known *Escherichia coli* UPRT gene sequence (GenBank accession X57104). These primers were homologous to the *Escherichia coli* sequences (forward: 5' TTT GTG GCT GCC CCT CAA AGG 3'; reverse: 5' AAA AGC CGA CTC TTA AAG TCG GCT T 3'), and proved unsuccessful in amplifying the *Salmonella* UPP gene from the purified genomic DNA in several attempts. The *Escherichia coli* UPP gene was then entered into a nucleotide BLAST search engine (http://www.ncbi.nlm.nih.gov/BLAST), which displayed 88% homology to a small portion of a *Salmonella* GenBank submission for the purN and purI gene sequences (accession U68765.1). Approximately 50% of the *Escherichia coli* UPP was present at the end of this *Salmonella* purN and purI sequence. By aligning the front half of the *Salmonella* UPP sequence with the back half of the *Escherichia coli* UPP sequence, a hypothetical UPP hybrid was constructed. PCR primers were then designed with a forward primer homologous to the *Salmonella* sequence (Forward-1: 5' TTT GTG GTT GCC AGT CAT CTG AGG 3'; Forward-2: 5' ATC CAG GTC AAG CAT ACA TTG TGT TG 3'; Forward-3: 5' AGG ATA TCC AGC ACT TGG TTT ACG AC 3') and several reverse primers homologous to the *Escherichia coli* sequences (Reverse-1: 5' CTG GAT CGC GCA GCA GAT CTT TTT T 3'; Reverse-2: 5' ATA AGC CGG AAT TTT CCC TTT 3'; Reverse-3: 5' CCC CGC TTT CTT CAC GAT AAA AGA AA 3'). These *Escherichia coli* primers were designed to prime homopolymeric runs in *Salmonella* to allow sufficient amplification by PCR based. Amplification from *Salmonella* TA100 yielded the PCR products of the predicted size, which were then sequenced to reveal the *Salmonella* UPP nucleotide sequence. Three independent cultures of TA100 were obtained from different sources, and the *Salmonella* UPP gene was amplified and sequenced to confirm the DNA sequence. The *Salmonella* UPP sequence demonstrated 88% homology to the *Escherichia coli* sequence at the nucleotide level, and 99% homology at the amino acid level.

The *Salmonella* uraA sequence was then determined using a similar approach. First, the *Escherichia coli* uraA sequence was obtained from GenBank (accession AE000336 U00096). Surprisingly, it was noted that the *Escherichia coli* UPP resides 86 nucleotides upstream from the uraA start codon. In the previously determined *Salmonella* UPP nucleotide sequence, approximately 800 nucleotides downstream from the UPP stop codon were determined, accounting for approximately half of the *Salmonella* uraA gene. *Salmonella* forward PCR primers were designed with homology to the determined *Salmonella* sequences (Forward-1: 5' AAA CCA CTC ATA ACA AAC ACA CTT AG 3'; Forward-2: 5' CGG TGT TCG GCT CCG TAC TGT 3'), and *Escherichia coli* reserve PCR primers were then designed to prime homopolymeric runs (Reverse-1: 5' CCT CAA CCA GGA TTT CAC AAA 3'; Reverse-2: 5' GCC AGT AAA GAG GAG TTA TCC CC 3'; Reverse-3: 5' CGG AAC AAA CCA GGT GCG TTT 3') in hopes of finding some level of homology to *Salmonella* to allow sufficient amplification by PCR.

PCR amplification was performed as follows: 94° C. for 2 minutes, followed by 32 cycles of 94° C. for 15 seconds, 50° C. for 30 seconds, 72° C. for 1 minute, ending with a 3 minute extension at 72° C. Amplification was successful, and the PCR products were then sequenced to reveal the *Salmonella* uraA nucleotide sequence. *Salmonella* uraA gene was amplified and sequenced from three independent cultures, and a consensus DNA sequence obtained. The *Salmonella* uraA sequence demonstrated 82% homology to the *Escherichia coli* sequence at the nucleotide level, and 93% homology at the amino acid level.

Upon determining the *Salmonella* UPP and uraA nucleic acid, several FU-resistant clones were isolated and the genomic DNA sequenced to confirm their role in the biochemical pathway of FU resistance. Genomic DNA was isolated from the FU-resistant clones as described above, both the UPP and uraA genes amplified by PCR, and PCR products sequenced. All clones analyzed contained molecular defects in the UPP gene, all altering the amino acid sequence of the protein, confirming that UPP is chiefly responsible for FU resistance in *Salmonella*.

While the invention has been described in detail with reference to certain preferred embodiments thereof, it will be understood that modifications and variations are within the spirit and scope of that which is described and claimed.

Summary of Sequences

Sequence ID NO. 1 is the combined nucleotide sequence of 2520 nucleobases that encodes a *Salmonella typhimurium* derived uracil transport protein (uraA protein) and the Uracil Phosphoribosyl Transferase protein (UPP/UPRT). The coding portion for the uraA is defined by nucleotides 929–2218, while the coding region of the UPRT gene is defined by nucleotides 215–841.

Sequence ID NO. 2 is the deduced amino acid sequence of the Uracil phosphoribosyltransferase protein.

Sequence ID NO. 3 is the deduced amino acid sequence of the Uracil Transport Protein.

What is claimed is:

1. An isolated nucleic acid molecule, comprising a sequence of nucleotides that encodes a uracil transport protein, wherein the sequence of nucleotides is selected from the group consisting of:
   (a) a sequence of nucleotides as set forth in SEQ ID NO:1;
   (b) a sequence of nucleotides that encode a protein having an amino acid sequence as set forth in SEQ ID NO:3;
   (c) a sequence of nucleotides degenerate with the uracil transport protein encoding sequence of (a) or (b).

2. The isolated nucleic acid molecule according to claim 1 wherein said nucleic acid molecule encodes a polypeptide comprising the amino acid sequence as set forth in SEQ ID NO:3.

3. The isolated nucleic acid molecule comprising the nucleotide sequence as set forth in SEQ ID NO:1.

4. An expression vector comprising a nucleic acid molecule comprising the sequence of nucleotides as set forth in SEQ ID NO:1, operably linked to a regulatory nucleotide sequence that controls expression of the nucleic acid molecule in a host cell.

5. Host cells transformed or transfected with the nucleic acid molecule of claim 4.

6. A method for identifying DNA sequences encoding a uracil transport protein of bacterial origin, the method comprising probing a cDNA library or a genomic library with a labeled probe comprising the nucleotide sequence of SEQ ID NO:1, and recovering from the library those sequences having a significant degree of homology relative to the probe.

7. A substantially pure polypeptide encoded by the nucleic acid molecule according to claim 1, which comprises the amino acid sequence as set forth in SEQ ID NO.3.

8. The nucleic acid molecule method according to claim 1, wherein the nucleic acid sequence comprises a coding region from nucleotides 215 to 841 of SEQ ID NO: 1.

* * * * *

SEQUENCE LISTING

<160> NUMBER OF SEQ ID NOS: 3

<210> SEQ ID NO 1
<211> LENGTH: 2520
<212> TYPE: DNA
<213> ORGANISM: Salmonella typhimurium

<400> SEQUENCE: 1

| | | | | | | |
|---|---|---|---|---|---|---|
| gggacaggtc | attcaccctt | aaaattgcta | atattcaaac | ggttgttagc | ctttatcgcc | 60 |
| tgtttcaacg | tgagtgattt | atactcactt | ttccgctatc | agcgcttttg | gttgatccag | 120 |
| gtcaagcata | cattgtgttg | cgtcagagag | gaaaagcggt | ataatccggc | gatttttttt | 180 |
| gtggttgcca | gtcatctgag | gataggagaa | gagtatgaag | atcgtggaag | tcaaacaccc | 240 |
| actcgtcaaa | cacaagctgg | gtctgatgcg | tgaaaacgac | attagcacta | aacgctttcg | 300 |
| tgaactcgcc | tcagaagtag | gcagcctgct | gacgtatgaa | gcgacagccg | acctggaaac | 360 |
| ggaaaaagtc | accatcgaag | gctggaatgg | cccggtggaa | atcgaccaga | tcaaaggtaa | 420 |
| aaaaattacc | gttgtgccga | ttctgcgcgc | gggtctgggt | atgatggaag | gcgttctgga | 480 |
| aaatgtaccg | agcgcgcgta | tcagcgtagt | cgggatgtac | cgtaacgaag | agacgcttga | 540 |
| gccagtacct | tatttccaga | aactggtatc | gaacattgat | gagcgcatgg | cgctgatcgt | 600 |
| cgacccgatg | ctggcgactg | gcggttctgt | catcgcgacc | atcgacctgc | tgaaaaaagc | 660 |
| aggctgtagc | agcattaagg | tgctggtgct | ggtcgccgcg | ccggaaggca | ttgcggcgct | 720 |
| ggaaaaagcg | caccgggacg | ttgaactgta | caccgcctct | atcgatcagg | ggcttaacga | 780 |
| gcacggatac | attattccgg | ggcttggcga | tgccggcgat | aagattttg | gtaccaaata | 840 |
| agtgaataaa | taattaaaag | ccgactttaa | gagtcggctt | tttttttgaat | aaaaccactc | 900 |
| ataacaaaca | cacttagagg | aaaacactat | gacgcgccgt | gctatcgggg | tgagtgaaag | 960 |
| accgccgctt | ttacagacaa | tcccgcttag | tttacagcac | cttttcgcca | tgtttggcgc | 1020 |
| gaccgtgctg | gtgccagttc | tgtttcatat | caatcccgcg | acggtgctgc | tgtttaacgg | 1080 |
| tatcggaacg | ttgctgtatc | tctttatctg | caaaggtaaa | attcctgcct | acctcggatc | 1140 |
| gagctttgcc | tttatttccc | cggtattact | gttgttgccg | ctgggttatg | aagtggcgct | 1200 |
| gggcggtttt | attatgtgcg | gcgtgttgtt | ctgtctggtc | tctttcatcg | ttaaaaaagc | 1260 |
| gggcaccggc | tggctggatg | tgatgttccc | gcctgcggca | atgggcgcaa | tcgttgccgt | 1320 |
| catcggtctg | gagctggctg | gcgtcgcggc | ggggatggcc | ggattactgc | ctgcgcaagg | 1380 |
| gcagtcgccg | gacacgaaaa | caattatcat | ctccatggtc | acgctggcgg | tgacggtgtt | 1440 |
| cggctccgta | ctgtttcgcg | gtttcctggc | gatcattccg | attttgatcg | gcgtgctggc | 1500 |
| gggctatgcg | ctgtcattcg | cgctgggggt | ggtcgatacc | acgccgattg | cccaggcgca | 1560 |
| ctggtttgcg | ctgccgacct | tctatacgcc | gcgttttgaa | tggttcgcga | tcctgacgat | 1620 |
| tctgcccgcg | gcgttggtcg | tgatcgccga | gcatgtcggt | catctggtgg | tgacggcgaa | 1680 |
| tatcgtcaaa | aaagatttag | tgcgcgatcc | cggtttgcac | cgctcgatgt | tcgctaacgg | 1740 |

```
actgtcgacg atcatttccg gtttcttcgg ctccacgccg aataccccct atggggaaaa    1800
tattggcgtc atggcgatca cccgcgttta cagtacctgg gttatcggcg gcgcggcgat    1860
tttcgccatt ctgctttcct gcgttggcaa actggcggcg gcgattcaga ttatcccgtt    1920
acccgtgatg ggcggcgtct cgctgctgtt gtacggcgtt atcggcgcgt cggggattcg    1980
cgtcttgatc gaatcgaaag tcgactacaa caaagcgcaa aacctgatcc tcacctcggt    2040
gattttgatc atcggcgtga gcggcgcgaa agtgcatatc ggcgcggcag aattgaaagg    2100
gatggcgctg gcgaccatcg tcgggatttg cctgagcctg atttttaaac tgattagcct    2160
gttgcgtccg gaagaagtgg tactggaggc aaatgatgcg gagcccccgc atcagtaacg    2220
ggttgccggg cagcgatgct gcccggttct atctcacggg aattatgtgg taaactcagc    2280
gcgattttat gtcatcctgg gttgaggtat ctctgaacac accggcacag ctctctttgc    2340
cactttatct tcctgacgac gaaactttcg caagtttctg gccggggat aacgcctctc     2400 tactggccgc gttacaaaac gtgttgcgcc aggaacatag tggatatatc tacctttggg    2460
cgcgtgaagg cgcgggccgc agccatttac tgcacgccgc ctgtgctgaa ctgtcgcagc    2520
```

<210> SEQ ID NO 2
<211> LENGTH: 208
<212> TYPE: PRT
<213> ORGANISM: Uracil Phosphoribosyl-transferase

<400> SEQUENCE: 2

```
Met Lys Ile Val Glu Val Lys His Pro Leu Val Lys His Lys Leu Gly
  1               5                  10                  15

Leu Met Arg Glu Asn Asp Ile Ser Thr Lys Arg Phe Arg Glu Leu Ala
             20                  25                  30

Ser Glu Val Gly Ser Leu Leu Thr Tyr Glu Ala Thr Ala Asp Leu Glu
         35                  40                  45

Thr Glu Lys Val Thr Ile Glu Gly Trp Asn Gly Pro Val Glu Ile Asp
     50                  55                  60

Gln Ile Lys Gly Lys Lys Ile Thr Val Val Pro Ile Leu Arg Ala Gly
 65                  70                  75                  80

Leu Gly Met Met Glu Gly Val Leu Glu Asn Val Pro Ser Ala Arg Ile
                 85                  90                  95

Ser Val Val Gly Met Tyr Arg Asn Glu Glu Thr Leu Glu Pro Val Pro
            100                 105                 110

Tyr Phe Gln Lys Leu Val Ser Asn Ile Asp Glu Arg Met Ala Leu Ile
        115                 120                 125

Val Asp Pro Met Leu Ala Thr Gly Gly Ser Val Ile Ala Thr Ile Asp
    130                 135                 140

Leu Leu Lys Lys Ala Gly Cys Ser Ser Ile Lys Val Leu Val Leu Val
145                 150                 155                 160

Ala Ala Pro Glu Gly Ile Ala Ala Leu Glu Lys Ala His Pro Asp Val
                165                 170                 175

Glu Leu Tyr Thr Ala Ser Ile Asp Gln Gly Leu Asn Glu His Gly Tyr
            180                 185                 190

Ile Ile Pro Gly Leu Gly Asp Ala Gly Asp Lys Ile Phe Gly Thr Lys
        195                 200                 205
```

<210> SEQ ID NO 3
<211> LENGTH: 429
<212> TYPE: PRT
<213> ORGANISM: Uracil Transport Protein

<400> SEQUENCE: 3

```
Met Thr Arg Arg Ala Ile Gly Val Ser Glu Arg Pro Pro Leu Leu Gln
 1               5                  10                  15

Thr Ile Pro Leu Ser Leu Gln His Leu Phe Ala Met Phe Gly Ala Thr
                20                  25                  30

Val Leu Val Pro Val Leu Phe His Ile Asn Pro Ala Thr Val Leu Leu
                35                  40                  45

Phe Asn Gly Ile Gly Thr Leu Leu Tyr Leu Phe Ile Cys Lys Gly Lys
         50                  55                  60

Ile Pro Ala Tyr Leu Gly Ser Ser Phe Ala Phe Ile Ser Pro Val Leu
 65                  70                  75                  80

Leu Leu Leu Pro Leu Gly Tyr Glu Val Ala Leu Gly Gly Phe Ile Met
                    85                  90                  95

Cys Gly Val Leu Phe Cys Leu Val Ser Phe Ile Val Lys Lys Ala Gly
                100                 105                 110

Thr Gly Trp Leu Asp Val Met Phe Pro Pro Ala Ala Met Gly Ala Ile
            115                 120                 125

Val Ala Val Ile Gly Leu Glu Leu Ala Gly Val Ala Ala Gly Met Ala
        130                 135                 140

Gly Leu Leu Pro Ala Gln Gly Gln Ser Pro Asp Thr Lys Thr Ile Ile
145                 150                 155                 160

Ile Ser Met Val Thr Leu Ala Val Thr Val Phe Gly Ser Val Leu Phe
                165                 170                 175

Arg Gly Phe Leu Ala Ile Pro Ile Leu Ile Gly Val Leu Ala Gly
                180                 185                 190

Tyr Ala Leu Ser Phe Ala Leu Gly Val Val Asp Thr Thr Pro Ile Ala
                195                 200                 205

Gln Ala His Trp Phe Ala Leu Pro Thr Phe Tyr Thr Pro Arg Phe Glu
        210                 215                 220

Trp Phe Ala Ile Leu Thr Ile Leu Pro Ala Ala Leu Val Val Ile Ala
225                 230                 235                 240

Glu His Val Gly His Leu Val Val Thr Ala Asn Ile Val Lys Lys Asp
                245                 250                 255

Leu Val Arg Asp Pro Gly Leu His Arg Ser Met Phe Ala Asn Gly Leu
                260                 265                 270

Ser Thr Ile Ile Ser Gly Phe Phe Gly Ser Thr Pro Asn Thr Thr Tyr
            275                 280                 285

Gly Glu Asn Ile Gly Val Met Ala Ile Thr Arg Val Tyr Ser Thr Trp
        290                 295                 300

Val Ile Gly Gly Ala Ala Ile Phe Ala Ile Leu Leu Ser Cys Val Gly
305                 310                 315                 320

Lys Leu Ala Ala Ala Ile Gln Ile Ile Pro Leu Pro Val Met Gly Gly
                325                 330                 335

Val Ser Leu Leu Leu Tyr Gly Val Ile Gly Ala Ser Gly Ile Arg Val
                340                 345                 350

Leu Ile Glu Ser Lys Val Asp Tyr Asn Lys Ala Gln Asn Leu Ile Leu
            355                 360                 365

Thr Ser Val Ile Leu Ile Ile Gly Val Ser Gly Ala Lys Val His Ile
        370                 375                 380

Gly Ala Ala Glu Leu Lys Gly Met Ala Leu Ala Thr Ile Val Gly Ile
385                 390                 395                 400

Cys Leu Ser Leu Ile Phe Lys Leu Ile Ser Leu Leu Arg Pro Glu Glu
                405                 410                 415
```

-continued

```
Val Val Leu Glu Ala Asn Asp Ala Glu Pro Pro His Gln
        420                 425
```